US012582381B1

(12) United States Patent (10) Patent No.: US 12,582,381 B1
Smith et al. (45) Date of Patent: Mar. 24, 2026

(54) ERGONOMIC ULTRASOUND SUPPORT

(71) Applicant: Hugh Smith, Welch, MN (US)

(72) Inventors: Hugh Smith, Welch, MN (US); J. Hunter Downs, III, Rochester, MN (US)

(73) Assignee: Hugh Smith, Welch, MN (US)

( * ) Notice: Subject to any disclaimer, the term of this patent is extended or adjusted under 35 U.S.C. 154(b) by 0 days.

(21) Appl. No.: 19/197,146

(22) Filed: May 2, 2025

Related U.S. Application Data

(60) Provisional application No. 63/773,342, filed on Mar. 17, 2025.

(51) Int. Cl.
     *A61B 8/00* (2006.01)
(52) U.S. Cl.
     CPC .................................. *A61B 8/4227* (2013.01)
(58) Field of Classification Search
     None
     See application file for complete search history.

(56) References Cited

U.S. PATENT DOCUMENTS

| | | | |
|---|---|---|---|
| 5,088,500 | A | 2/1992 | Wedel et al. |
| 5,752,517 | A | 5/1998 | Harman et al. |
| 5,897,503 | A | 4/1999 | Lyon et al. |
| 8,118,747 | B2 | 2/2012 | Furia et al. |
| 2005/0085731 | A1 | 4/2005 | Miller et al. |
| 2006/0173331 | A1 | 8/2006 | Booton et al. |
| 2007/0066894 | A1 | 3/2007 | Bartol et al. |
| 2008/0051662 | A1* | 2/2008 | Kliewer .............. A61B 8/4281 |
| | | | 600/459 |
| 2008/0146936 | A1 | 6/2008 | Furia et al. |
| 2009/0163807 | A1 | 6/2009 | Sliwa |

(Continued)

FOREIGN PATENT DOCUMENTS

| | | |
|---|---|---|
| WO | 2010/059221 A2 | 5/2010 |
| WO | 2025/024191 A1 | 1/2025 |

OTHER PUBLICATIONS

Doss, William, "3 ways to reduce overuse injury in sonographers," Radiology Business, Sep. 7, 2016, Innovate Healthcare.

(Continued)

*Primary Examiner* — Yi-Shan Yang
(74) *Attorney, Agent, or Firm* — Headland Law & Strategy; Matthew J. Smyth

(57)                    ABSTRACT

A body-mounted support for an ultrasound transducer may include a forearm cradle, a transducer anchor and a beam that connects the transducer anchor to the forearm cradle. The forearm cradle may have the shape of a generally segmented cylinder, and it may be sized to accommodate a forearm of a user. The forearm cradle may include a dorsal portion configured to contact a dorsal portion of the user's upper forearm and a ventral portion configured to contact a ventral portion of the user's lower forearm. The forearm cradle may be characterized by a longitudinal cradle axis. The transducer anchor may include a backplate and retaining strap. The beam may also be characterized by a longitudinal beam axis. The longitudinal beam axis may be generally parallel to the longitudinal cradle axis and may be disposed below, relative to the forearm cradle, the longitudinal cradle axis.

7 Claims, 4 Drawing Sheets

(56) References Cited

U.S. PATENT DOCUMENTS

| | | | |
|---|---|---|---|
| 2012/0109019 A1* | 5/2012 | Schneider | A61N 7/00 |
| | | | 601/2 |
| 2013/0263438 A1 | 10/2013 | Burns et al. | |
| 2015/0265243 A1 | 9/2015 | Kelly | |
| 2018/0110497 A1 | 4/2018 | Beacham et al. | |
| 2019/0076121 A1 | 3/2019 | Southard et al. | |
| 2023/0293150 A1 | 9/2023 | Fuson | |
| 2023/0371925 A1 | 11/2023 | Pollock et al. | |

OTHER PUBLICATIONS

Ergonomic Probe, CIVCO Medical Solutions, https://www.civco.com/products/accessories/ergonomic-probe-grip/ (accessed Feb. 21, 2025).
Flexible Ureteroscope Stabilization Arm, Mediflex Surgical Products, https://mediflex.com/products/flexible-ureteroscope-stabilization-arm (accessed Feb. 21, 2025).
Swerdlow, Daniel R. et al., "Robotic Arm-Assisted Sonography: Review of Technical Developments and Potential Clinical Applications," AJR:208, Apr. 2017.
Murphey, Susan, "Work Related Musculoskeletal Disorders In Sonography," Society of Diagnostic Medical Sonography, 2021, Plano, Texas.

* cited by examiner

ERGONOMIC ULTRASOUND SUPPORT

CROSS REFERENCE TO RELATED APPLICATIONS

This application claims priority to U.S. Provisional Application Ser. No. 63/773,342, titled "Ergonomic Ultrasound Support," filed on Mar. 17, 2025. This application incorporates the entire contents of the foregoing application herein by reference.

TECHNICAL FIELD

Various implementations relate generally to supports for ultrasound transducers, particularly body-mounted supports.

BACKGROUND

Ultrasound sonographers are at risk of experiencing work-related musculoskeletal disorders (WRMSDs). One study indicated that 90% of clinical sonographers experience symptoms of WRMSDs. Risks for WRMSDs include forces required to be exerted by a sonographer on an ultrasound transducer to acquire clear images, especially with obese patients; repetitive motions and awkward positions often required for image capture; and other factors. Carpal and cubital tunnel syndrome, epicondylitis of the elbow, shoulder capsulitis and tendonitis, and neck and back strain may be common.

SUMMARY

Described herein are apparatuses and methods for minimizing, for ultrasound sonographers, strains that may increase the risk of WRMSDs. In some implementations, an apparatus minimizes strain on a sonographer's wrist by allowing transfer of force to an ultrasound transducer from the sonographer's forearm, without straining the wrist, or with minimal strain on the wrist outside of a neutral position.

A body-mounted support for an ultrasound transducer may include a forearm cradle, a transducer anchor having a backplate and retaining strap, and a beam that connects the transducer anchor to the forearm cradle. The beam may be characterized by a longitudinal beam axis. The forearm cradle may have a generally segmented cylindrical shape and be sized to accommodate a forearm of a user. The forearm cradle may include a dorsal portion configured to contact a dorsal portion of the user's upper forearm and a ventral portion configured to contact a ventral portion of the user's lower forearm. The forearm cradle may be characterized by a longitudinal cradle axis. The longitudinal beam axis may be generally parallel to the longitudinal cradle axis and may be disposed below, relative to the forearm cradle, the longitudinal cradle axis.

The body-mounted support may further include at least one of a ventral-portion strap or a dorsal-portion strap. The at least one of the ventral-portion strap or the dorsal-portion strap may include a resilient and elastic band. The at least one of the ventral-portion strap or the dorsal-portion strap may include a length-adjustment mechanism. The length-adjustment mechanism may include at least one of a hook-and-loop system or a peg-and-hole compression-fit closure system. The transducer anchor may further include a contoured support configured to cradle a cord associated with the transducer.

The forearm cradle, the transducer anchor and the beam may be configured such that the user can grasp a transducer that is disposed in the transducer anchor while the user's wrist is in a substantially neutral position. The forearm cradle, the transducer and the beam may be configured such that when the user's forearm is disposed in the forearm cradle and a transducer is disposed in the transducer anchor with a physical longitudinal axis of the transducer disposed parallel to the backplate, force exerted by the user on the ventral portion is transferred to the transducer along the physical longitudinal axis.

An adaptive handle for an ultrasound transducer may include a forearm cradle configured to conformably contact an upper surface of a sonographer's forearm. The forearm cradle may have a curved width that is perpendicular to a longitudinal axis of the forearm cradle and a first side and a second side. A first beam may extend on the first side and a second beam may extend on the second side. Each of the first beam and second beam may terminate at opposite sides of a base of a transducer retention loop. A thenar rest may be coupled to the transducer retention loop, the first beam and the second beam. A diameter of the transducer retention loop may be adjustable. The forearm cradle may comprise a material having a first stiffness value and each of the first beam and the second beam may comprise a material having a second stiffness value that is greater than the first stiffness value. The transducer retention loop may comprise a material that is inherently elastic and resilient, such that the diameter can be adjusted by extension of the material. The transducer retention loop may include a size-adjustable closure mechanism.

DETAILED DESCRIPTION

Described herein are apparatuses and methods for minimizing, for ultrasound sonographers, strains that may increase the risk of WRMSDs. In some implementations, an apparatus minimizes strain on a sonographer's wrist by allowing transfer of force to an ultrasound transducer from the sonographer's forearm, without straining the wrist, or with minimal strain on the wrist outside of a neutral position.

Figure 1A:
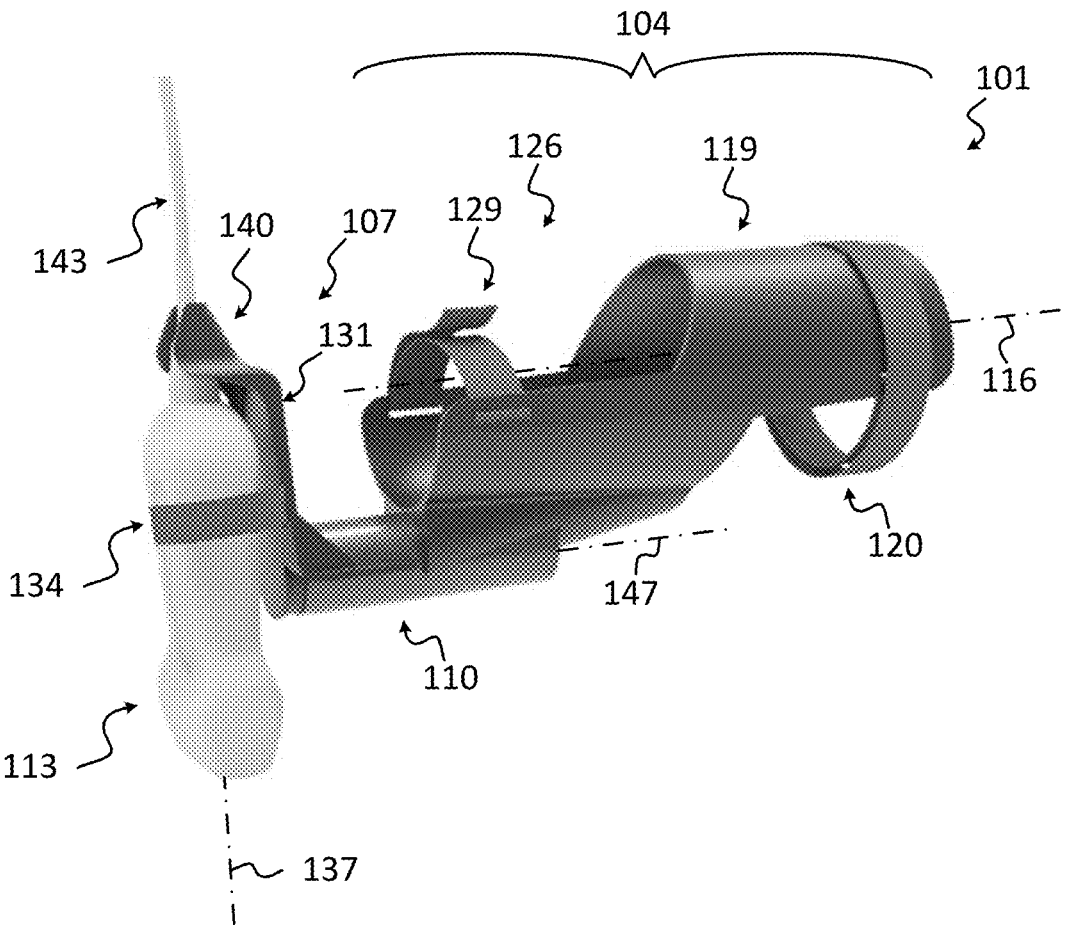
FIG. 1A illustrates an exemplary body-mounted support.

FIG. 1A illustrates an exemplary body-mounted support 101. In the implementation shown, the body-mounted support 101 includes three elements: a forearm cradle 104, a transducer anchor 107 and a beam 110 that couples the forearm cradle 104 to the transducer anchor 107. The transducer anchor 107 may be configured to secure an ultrasound transducer 113.

Figure 1B:
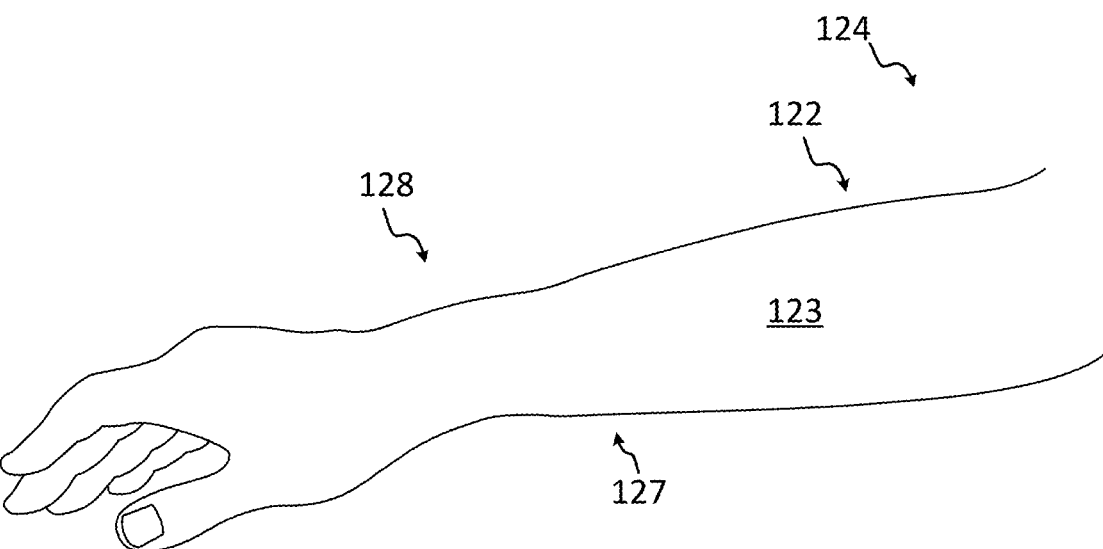
FIG. 1B illustrates portions of a user's forearm that may engage with the exemplary body-mounted support of FIG. 1A.

In some implementations, the forearm cradle 104 has a segmented, generally cylindrical shape that is configured to accommodate a user's forearm (see FIG. 1B). The forearm cradle 104 may be characterized by a longitudinal axis 116. It may have a dorsal portion 119 that is configured to contact a dorsal portion 122 a user's forearm 123 (e.g., specifically, the user's upper forearm 124) and a ventral portion 126 that is configured to contact a ventral portion 127 of the user's lower forearm 128.

In some implementations, the dorsal portion 119 includes a dorsal-portion strap 120 that is configured to secure the dorsal portion 119 to the user's forearm 123, and the ventral portion 126 includes a ventral-portion strap 129 that is configured to secure the ventral portion 126 to the user's forearm 123. In some implementations, only one strap 120 or 129 may be provided; in still other implementations, straps 120 and 129 may be omitted. When provided, straps 120 or 129 may include length-adjusting mechanisms or properties similar to those described below with reference to the retaining strap 134.

The transducer anchor 107 may include a backplate 131 and a retaining strap 134. The retaining strap 134 may have an adjustable length and may be configured to secure the ultrasound transducer 113 against the backplate 131. For example, in some implementations, the retaining strap 134 may be made of an elastic and resilient material that may be stretched around the ultrasound transducer. In other implementations, other length-adjusting mechanisms may be employed (e.g., a retaining slot or channel configured to secure a strap that includes a hook-and-loop fastener, or a peg-and-hole compression-fig closure system).

As shown, the transducer anchor 107 may be configured to retain the ultrasound transducer 113 such that a physical longitudinal axis 137 of the ultrasound transducer 113 is parallel to the backplate 131. In some implementations, the transducer anchor 107 may further include a contoured support 140 that accommodates a cord 143 associated with the transducer 113 and further secures, in conjunction with the retaining strap 134, the ultrasound transducer 113 to the transducer anchor 107.

The beam 110 that couples the forearm cradle 104 to the transducer anchor 107 may be characterized by a longitudinal axis 147, which, in some implementations, may be substantially parallel to the longitudinal axis 116 and substantially perpendicular to the backplate 131. (In this context, "substantially" may mean within 1%, or 5%, or 10%, or 20% of a nominal value or position; "about" or "approximately" may have a similar meaning—e.g., within 1%, or 5%, or 10%, or 20%, or 50%, or 100% of a nominal value.) In some implementations, as shown, the longitudinal axis 147 of the beam 110 may be disposed lower than the longitudinal axis 116 of the forearm cradle 104, such that the ultrasound transducer 113 extends below the beam 110 and forearm cradle 104.

Figure 2A:
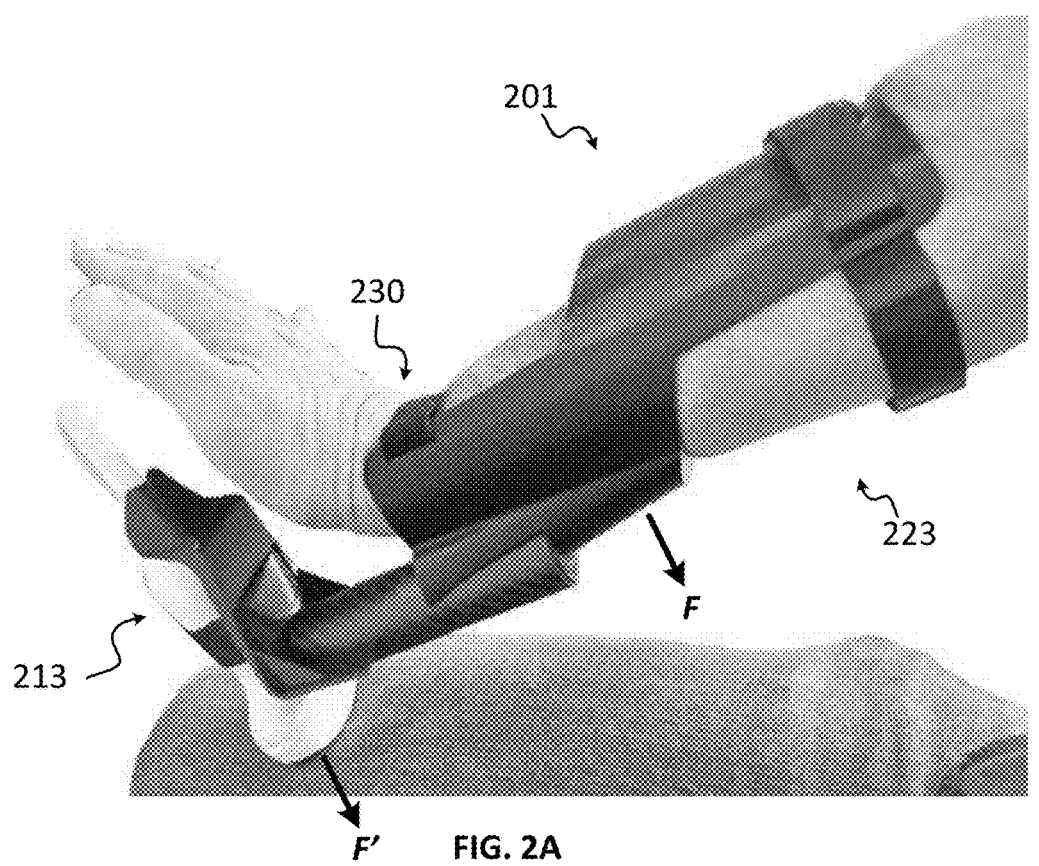
FIGS. 2A and 2B depict an exemplary body-mounted support in use.
Figure 2B:
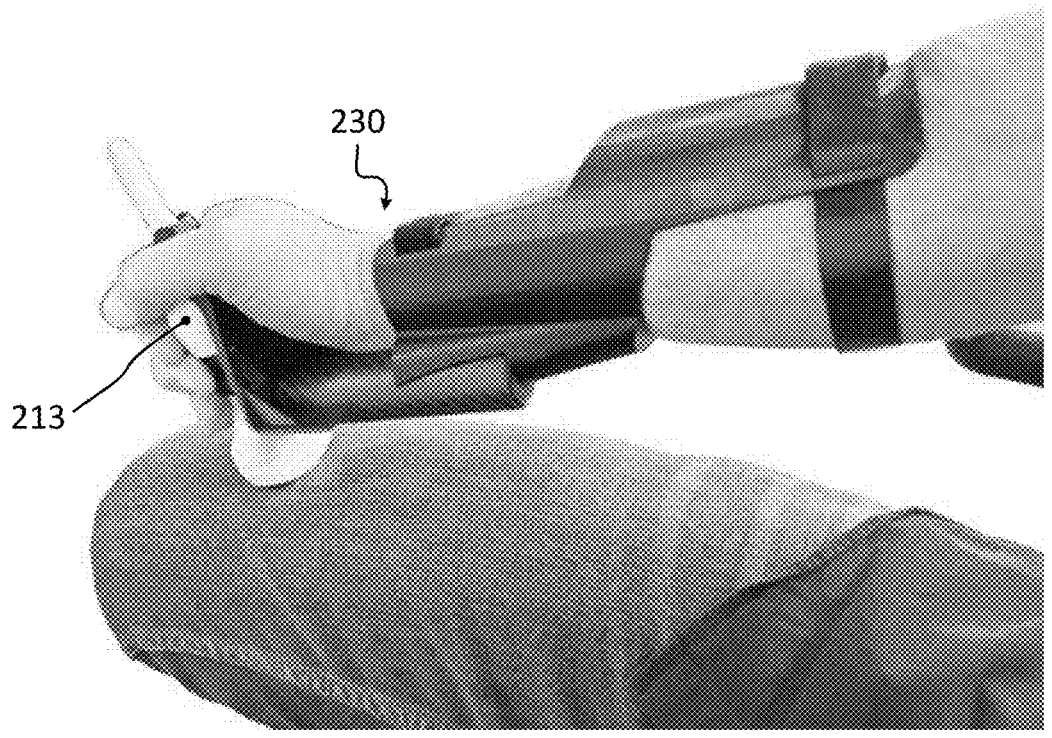

FIG. 2A illustrates an exemplary body-mounted support 201 in use. In particular, the body-mounted support 201 is strapped to a user's forearm 223, and an ultrasound transducer 213 is affixed to the body-mounted support 201. In such a configuration, a force F, exerted by the user's forearm 223, may be transferred to the ultrasound transducer 213 as a force F'—without that force being exerted on or through the user's wrist 230. Moreover, as shown in FIG. 2B, the user may grasp the ultrasound transducer 213 with his or her wrist 230 in a substantially neutral position, without having to exert force through the wrist 230.

Figure 3A:
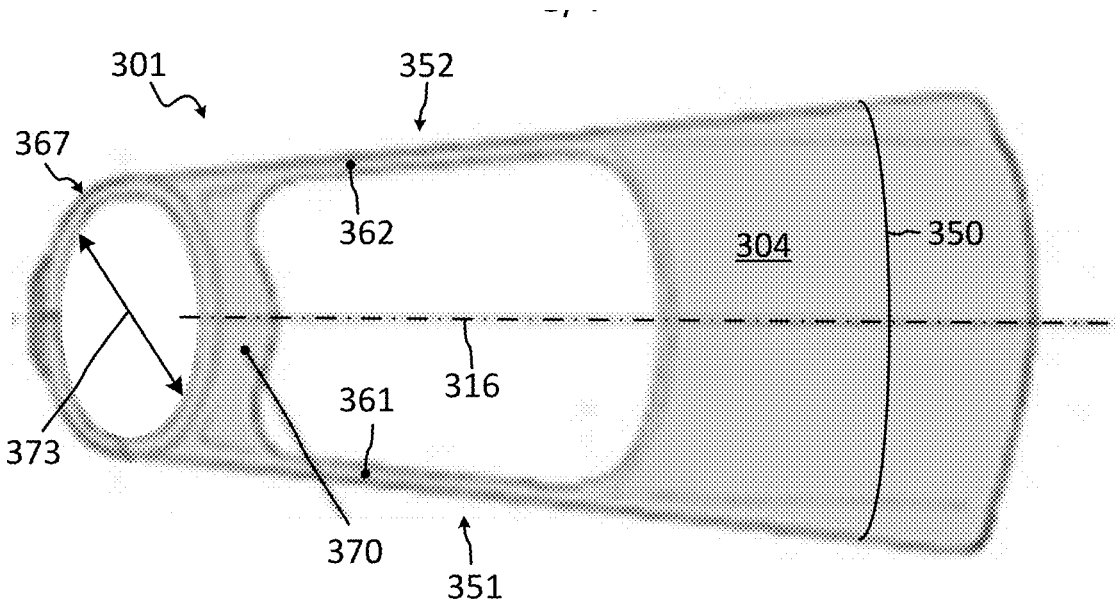
FIGS. 3A and 3B illustrate an exemplary adaptive handle.
Figure 3B:
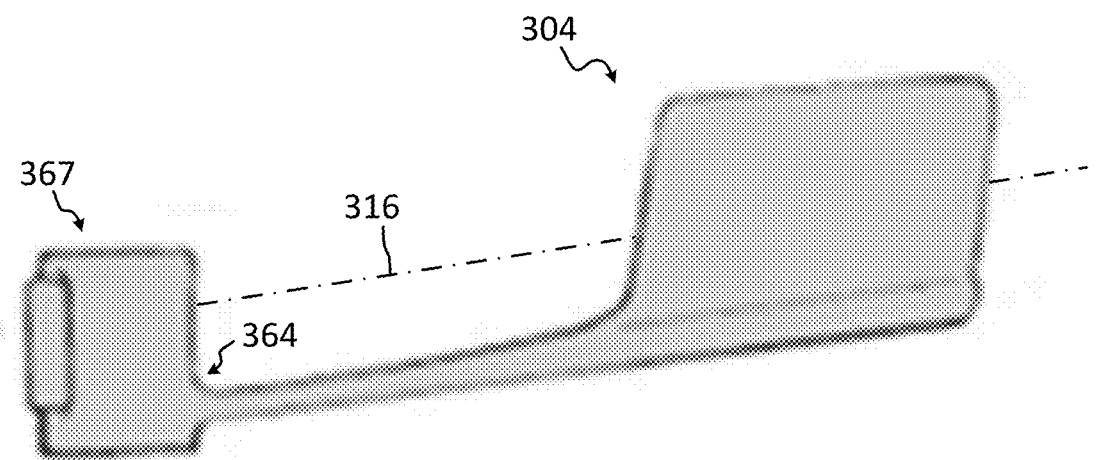

FIGS. 3A and 3B illustrate an exemplary adaptive handle 301 for an ultrasound transducer. As shown, the adaptive handle 301 may include a forearm cradle 304 that is configured to conformably contact an upper surface of a sonographer's forearm (see FIGS. 3C and 3D). The forearm cradle 304 may be characterized by a longitudinal axis 316 and may have a curved width 350 that is substantially perpendicular to the longitudinal axis 316. The forearm cradle 304 may further include a first side 351 and a second side 352, each of which may be substantially parallel to the longitudinal axis 316. A first beam 361 may extend along the first side 351, and a second beam 362 may extend along the second side 352. Each of the first beam 361 and second beam 361 may terminate at opposite sides of a base 364 of a transducer retention loop 367. A thenar rest 370 may be coupled to the transducer retention loop 367, the first beam 361 and the second beam 362. A diameter 373 of the transducer retention loop may be adjustable (e.g., in a manner as described above with respect to other implementations).

In some implementations, the forearm cradle 304 may be made of a material having a first stiffness value (e.g., a silicone having a Shore A durometer in the range of about 20 to about 50) and the first beam 361 and second beam 362 may be made of a different material having a second stiffness value that is greater than the first stiffness value. Alternatively, the first beam 361 and the second beam 362 may be made of the same material as the other portions of the forearm cradle 304, but the stiffness properties may be greater (e.g., a silicone having a Shore A durometer in the range of about 50 to about 100).

Figure 3C:
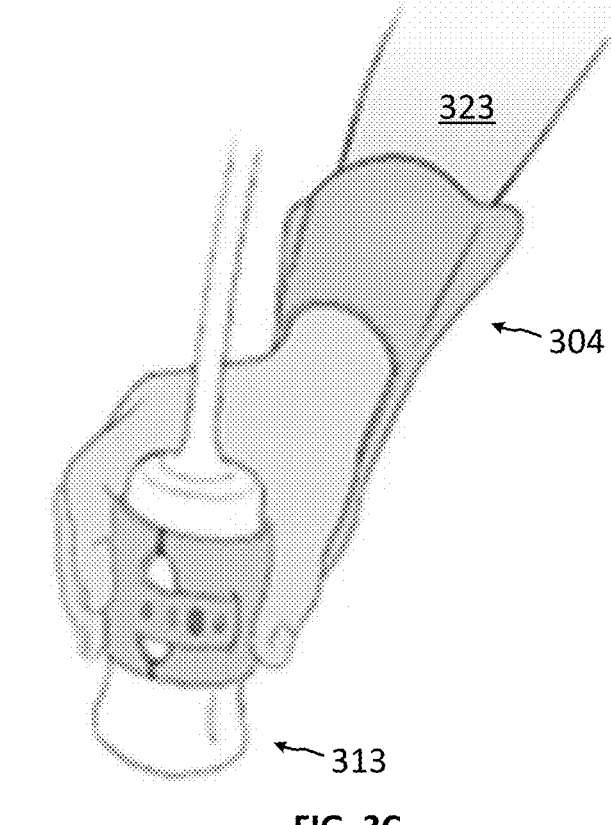
FIGS. 3C and 3D depict, in use, the exemplary adaptive handle shown in FIGS. 3A-3B.
Figure 3D:
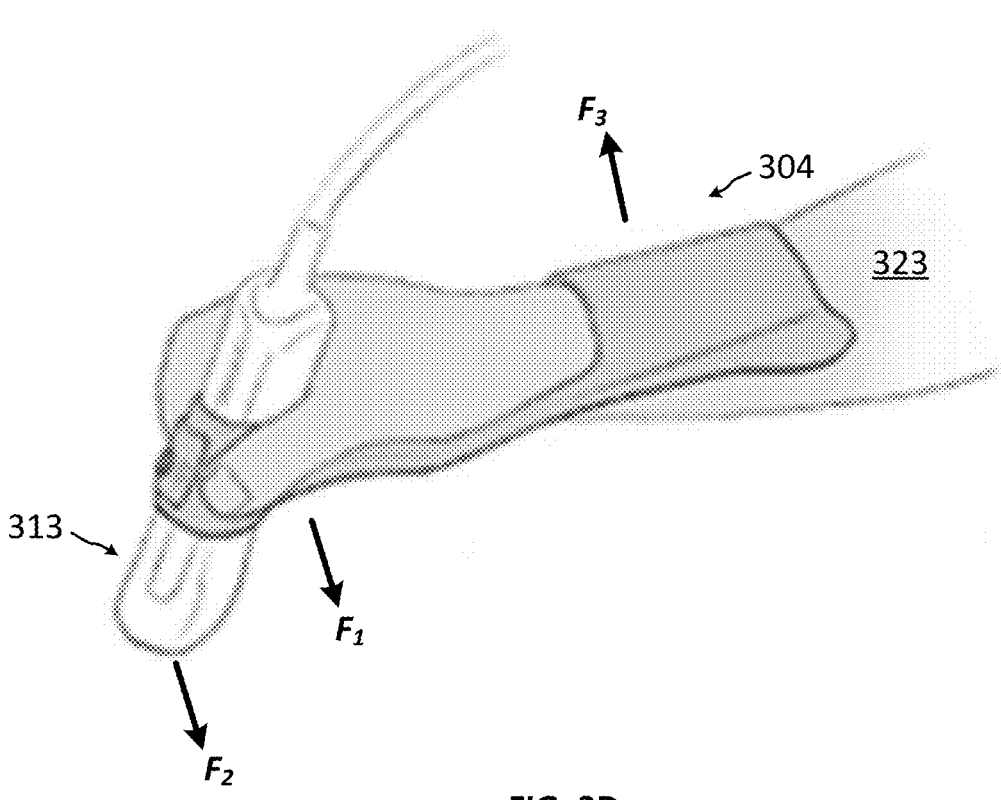

FIGS. 3C and 3D illustrate the exemplary adaptive handle 301 in use. As shown, a user's arm 323 may rest in the forearm cradle 304, and a thenar portion of the user's hand may rest on the thenar rest 370 (not visible in FIGS. 3C and 3D). In such a configuration, a user may exert a downward force $F_1$ on the thenar rest 370 while the user's wrist is in a substantially neutral position, and such force may be transferred to the ultrasound transducer 313 as a corresponding force $F_2$. A user may exert an upward force $F_3$ on his or her forearm 323 to raise the ultrasound transducer 313, without having to tightly grip the ultrasound transducer 313.

Several implementations have been described with reference to exemplary aspects, but it will be understood by those skilled in the art that various changes may be made and equivalents may be substituted for elements thereof without departing from the contemplated scope. For example, various materials may be employed (e.g., silicones of various hardness values, plastics, rubbers, other polymers); different hardness materials than those specified may be employed; different, well-known length-adjusting mechanisms may be employed; various numbers of straps may be employed to hold an adaptor or support to a user's arm; other retention mechanisms in lieu of straps may be employed, such as elastic sleeves; different orientations may be employed (e.g., an ultrasound transducer anchor may be disposed at an angle relative to a forearm longitudinal axis, rather than being in line with such an axis).

Many other variations are possible, and modifications may be made to adapt a particular situation or material to the teachings provided herein without departing from the essential scope thereof. Therefore, it is intended that the scope include all aspects falling within the scope of the appended claims.

What is claimed is:

1. A body-mounted support for an ultrasound transducer, comprising:

a forearm cradle having a substantially segmented cylindrical shape and being sized to accommodate a forearm of a user, the forearm cradle comprising a dorsal surface configured to contact a dorsal portion of the user's upper forearm and a ventral surface configured to contact a ventral portion of the user's lower forearm, the forearm cradle being characterized by a longitudinal cradle axis;

a ventral-surface strap disposed directly opposite the ventral surface and a dorsal-surface strap disposed directly opposite the dorsal surface;

a transducer anchor comprising a backplate and retaining strap; and a beam that connects the transducer anchor to the forearm cradle, the beam being characterized by a longitudinal beam axis;

wherein, the longitudinal beam axis is substantially parallel to the longitudinal cradle axis and disposed below, relative to the forearm cradle, the longitudinal cradle axis.

2. The body-mounted support of claim 1, wherein at least one of the ventral-surface strap or the dorsal-surface strap comprises a resilient and elastic band.

3. The body-mounted support of claim 1, wherein at least one of the ventral-surface strap or the dorsal-surface strap comprises a length-adjustment mechanism.

4. The body-mounted support of claim 3, wherein the length-adjustment mechanism comprises at least one of a hook-and-loop system or a peg-and-hole compression-fit closure system.

5. The body-mounted support of claim 1, wherein the transducer anchor further comprises a contoured support configured to cradle a cord associated with the transducer.

6. The body-mounted support of claim 1, wherein the forearm cradle, the transducer anchor and the beam are configured such that the user can grasp a transducer that is disposed in the transducer anchor while the user's wrist is in a substantially neutral position.

7. The body-mounted support of claim 1, wherein the forearm cradle, the transducer and the beam are configured such that when the user's forearm is disposed in the forearm cradle and a transducer is disposed in the transducer anchor with a physical longitudinal axis of the transducer disposed parallel to the backplate, force exerted by the user on the ventral portion is transferred to the transducer along the physical longitudinal axis.

* * * * *